United States Patent
Knappe et al.

(10) Patent No.: US 11,234,922 B2
(45) Date of Patent: Feb. 1, 2022

(54) COSMETIC AGENT FOR TEMPORARILY RESHAPING KERATINOUS FIBRES WITH FILM FORMER

(71) Applicant: Henkel AG & Co. KGaA, Duesseldorf (DE)

(72) Inventors: Thorsten Knappe, Schenefeld (DE); Marie Meisel, Hemslingen (DE); Laura Meunier, St. Germain-en-laye (FR)

(73) Assignee: HENKEL AG & CO. KGAA, Duesseldorf (DE)

( * ) Notice: Subject to any disclaimer, the term of this patent is extended or adjusted under 35 U.S.C. 154(b) by 23 days.

(21) Appl. No.: 16/220,921

(22) Filed: Dec. 14, 2018

(65) Prior Publication Data

US 2019/0183774 A1  Jun. 20, 2019

(30) Foreign Application Priority Data

Dec. 15, 2017 (DE) ..................... 10 2017 222 851.2

(51) Int. Cl.
| | |
|---|---|
| *A61K 8/73* | (2006.01) |
| *A61K 8/81* | (2006.01) |
| *A61K 8/31* | (2006.01) |
| *B05B 9/04* | (2006.01) |
| *A61Q 5/06* | (2006.01) |
| *A61K 8/365* | (2006.01) |
| *A61K 8/86* | (2006.01) |
| *A61K 8/92* | (2006.01) |

(52) U.S. Cl.
CPC ............... *A61K 8/732* (2013.01); *A61K 8/31* (2013.01); *A61K 8/365* (2013.01); *A61K 8/736* (2013.01); *A61K 8/8158* (2013.01); *A61K 8/86* (2013.01); *A61K 8/922* (2013.01); *A61Q 5/06* (2013.01); *B05B 9/04* (2013.01); *A61K 2800/594* (2013.01)

(58) Field of Classification Search
CPC ........ A61K 8/732; A61K 8/8158; A61K 8/31; A61K 8/922; A61K 8/736; A61K 8/365; A61K 8/86; A61K 2800/594; A61Q 5/06; B05B 9/04
See application file for complete search history.

(56) References Cited

U.S. PATENT DOCUMENTS

| | | | | |
|---|---|---|---|---|
| 8,603,447 | B2 * | 12/2013 | Mueller | A61K 8/8152 424/70.11 |
| 8,609,078 | B2 * | 12/2013 | Schweinsberg | A61K 8/732 424/70.13 |
| 8,790,628 | B2 * | 7/2014 | Schweinsberg | A61K 8/046 424/70.13 |
| 9,168,217 | B2 * | 10/2015 | Schweinsberg | A61Q 5/10 |
| 2006/0236469 | A1 * | 10/2006 | Bone | A61K 8/22 8/405 |
| 2012/0201774 | A1 * | 8/2012 | Schweinsberg | A61K 8/732 424/70.13 |
| 2012/0213724 | A1 * | 8/2012 | Mueller | A61K 8/046 424/70.13 |
| 2014/0290686 | A1 | 10/2014 | Schweinsberg | |
| 2017/0246100 | A1 | 8/2017 | Puls | |

FOREIGN PATENT DOCUMENTS

WO   2016065439 A1   5/2016

OTHER PUBLICATIONS

Product data sheet for Hydagen HCMF; 2011.*

* cited by examiner

*Primary Examiner* — Blessing M Fubara
(74) *Attorney, Agent, or Firm* — Lorenz & Kopf, LLP

(57) ABSTRACT

The application describes a cosmetic agent for temporarily reshaping keratin fibres, in particular human hair, comprising a film former and a cosmetic carrier, wherein the film former comprises
  at least one neutralization product of chitosan with at least one organic acid and
  at least one non-ionic propylene oxide-modified starch,
which cosmetic agent is also substantially free of a fully synthetic film former.

17 Claims, No Drawings

COSMETIC AGENT FOR TEMPORARILY RESHAPING KERATINOUS FIBRES WITH FILM FORMER

CROSS-REFERENCE TO RELATED APPLICATION

This application claims priority to German Patent Application No. 10 2017 222 851.2, filed Dec. 15, 2017, which is incorporated herein by reference in its entirety.

TECHNICAL FIELD

The present disclosure relates to cosmetic agents for temporarily reshaping keratinous fibres, comprising a film former and a cosmetic carrier.

BACKGROUND

Cosmetic agents used to permanently or temporarily shape the hair play an important role in the field of cosmetics. Temporary shaping with a good hold without compromising the healthy appearance of the hair, such as the shine thereof, can be attained for example by hairsprays, hair waxes, hair gels, hair mousses, blow drying, etc.

The most important property of an agent for temporarily shaping keratin fibres lies in providing the treated fibres with the greatest possible hold in the produced form. If the keratin fibres are human hair, reference is also made to a strong hairstyle hold or to a high holding power of the cosmetic agent. The hold of a hairstyle is determined fundamentally by the type and quantity of the polymers used.

In the prior art, numerous cosmetic agents are known which provide temporary shaping. Corresponding agents usually contain synthetic polymers as shaping components. Preparations which contain a dissolved or dispersed polymer can be applied to the hair by employing a propellant gas or by a pump mechanism. Hair gels and hair waxes are by contrast generally not applied directly to the hair, but instead distributed in the hair by employing a comb or using the hands.

The synthetic polymers usually used in agents for temporary shaping are produced from corresponding synthetically accessible monomers. Said monomers are recovered from fossil substances, such as petroleum, by conversion into the corresponding polymer building block, inter alia with a high energy consumption. Since the monomers are already produced synthetically, the polymers usually used are fully synthetic polymers. Within the scope of a conservation of raw materials and energy, it remains desirable to use, for cosmetic products, only cosmetic raw materials that are accessible from renewable raw materials with minimal energy consumption. A reduction in amount or even a complete replacement of said fully synthetic polymers can be implemented, however, only if the replacement polymers bring about the properties desired for the intended application and give the keratinous fibres a sufficient, stable hold in the styled form.

Numerous further properties that the cosmetic agent must bestow on the hair must still be maintained nevertheless with a reduction in amount or replacement of fully synthetic polymers. Cosmetic agents are thus intended to give the hair volume, and the bounce and silkiness of the keratinous fibres fixed in the form should be maintained. The formation of polymer particles visible with the naked eye on the keratinous fibres must be avoided. Furthermore, the keratinous fibres must not look dull, but instead should appear to have a natural shine. These and further properties that the cosmetic agent provides the hair with shall be referred to hereinafter as styling properties. The development of cosmetic agents that have all desired styling properties in combination still poses difficulties. In particular, this is true for the combination of a strong hold on the one hand and simple, uniform application to the keratinous fibres on the other hand.

The object forming the basis of the present disclosure lies in providing a cosmetic agent which is suitable for temporarily reshaping keratinous fibres, in which the use of fully synthetic polymers is significantly reduced or in which the use of fully synthetic polymers is omitted, wherein the styling properties are to be maintained at a high level. In particular, the polymers giving the hair the stable hold should not be fully synthetic polymers.

The object forming the basis of the present disclosure is achieved by the subject matter of claim 1. A first subject of the present disclosure is therefore a cosmetic agent for temporarily reshaping keratinous fibres, in particular human hair, comprising a film former and a cosmetic carrier, wherein the film former comprises at least one neutralization product of chitosan with at least one organic acid, and at least one non-ionic propylene oxide-modified starch, exemplified in that the cosmetic agent is substantially free from fully synthetic film formers. In a preferred embodiment of the present disclosure the cosmetic agent comprises a film former and a cosmetic carrier, wherein the film former substantially comprises at least one neutralization product of chitosan with at least one organic acid and also at least one non-ionic propylene oxide-modified starch.

BRIEF SUMMARY

Cosmetic agents and methods for temporarily reshaping keratin fibers are provided. In an exemplary embodiment, a cosmetic agent comprises a film former and a cosmetic carrier. The film former comprises at least one neutralization product of chitosan with at least one organic acid, and at least one non-ionic propylene oxide-modified starch. The cosmetic agent is substantially free from a fully synthetic film former.

In another embodiment, a method for temporarily reshaping keratin fibers is provided. The method includes applying a cosmetic agent to the keratin fibers, where the cosmetic agent comprises a film former and a cosmetic carrier. The film former comprises (a) at least one neutralization product of chitosan with at least one organic acid, and (b) at least one non-ionic propylene oxide-modified starch.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In accordance with the present disclosure the cosmetic agent comprises a film former. A film former is understood to mean polymers which, as they dry, leave behind a continuous film on the skin, the hair or the nails. Film formers of this kind can be used in a wide range of cosmetic products, such as face masks, make-up, hair fixers, hairsprays, hair gels, hair waxes, hair conditioners, shampoos or nail varnishes. Polymers that are sufficiently soluble in water, alcohol or water/alcohol mixtures are preferred. Corresponding solutions can thus be produced which can be applied or further processed in a simple way.

Within the scope of the present disclosure a film former is understood in particular to mean polymers which, when used in from about 0.05 to about 20% by weight (in relation to the total weight of the cosmetic agent) aqueous, alcoholic or aqueous-alcoholic solution, are capable of being depositing on the hair in the form of a transparent polymer film.

Within the scope of the present disclosure it is particularly important that the film former comprises two components. A first component is a neutralization product of chitosan with an organic acid. The organic acid is preferably a carboxylic acid. A second component is a non-ionic propylene oxide-modified starch. Both polymer constituents are based on renewable raw materials which are processed so as to be usable as film formers in the cosmetic agent.

The cosmetic agent of the present disclosure should comprise substantially no fully synthetically produced polymers used conventionally as film formers. Within the scope of the present disclosure, a film former is then deemed to be produced fully synthetically if all of the monomers constructing the film former are conventionally produced synthetically. Examples of fully synthetically produced film formers comprise in particular copolymers based on acrylate or methacrylate, in particular those that comprise, as monomer constituent, acrylic acid, methacrylic acid, alkyl(meth)acrylate, hydroxyalkyl(meth)acrylate or maleic acid anhydride; and copolymers which comprise, as monomer constituents, N-vinylpyrrolidones, alkylvinyl ethers with alkyl groups comprising from 1 to about 18 carbon atoms and/or vinyl esters of carboxylic acids with from 2 to about 18 carbon atoms, in particular polyvinylpyrrolidone/vinyl acetate copolymers; and also polyvinylpyrrolidone, wherein copolymers are understood to mean polymers that include two or more different monomers, and wherein all alkyl groups of the aforesaid monomers can also be branched and/or alkyl groups substituted with functional groups.

It has surprisingly been found that a cosmetic agent which is substantially free of fully synthetic film formers or which includes substantially the above first and the above second component can be formulated without necessarily having to accept any losses in respect of the styling properties. Within the scope of the present disclosure, the cosmetic agent can comprise up to about 0.05% by weight of fully synthetic polymers which are film formers in the conventional sense, so as to be "substantially" free of fully synthetic film formers. The cosmetic agent can preferably also be free of fully synthetic film formers, i.e. the cosmetic agent comprises about 0% by weight of fully synthetic film formers.

The film former of the cosmetic agent should preferably "substantially" comprise the two above components. Within the scope of the present disclosure this can preferably also mean that the film former of the cosmetic agent consists of the two above components exclusively, i.e. to an extent of about 100% by weight in relation to the total weight of the film former. The feature in accordance with which the film former of the cosmetic agent "substantially" comprises the two components shall be understood by a person skilled in the art such that further components can be present in the cosmetic agent in a small amount, for example up to about 1% by weight, preferably about 0.5% by weight, in relation to the total weight of the cosmetic agent and can be part of the polymer film, but without being film formers in the conventional sense. In other words, the film formed from the film former can also contain further constituents.

Within the scope of the present disclosure, "keratin fibres" shall be understood to mean fur, wool, feathers and in particular human hair.

Chitosans are biopolymers and are included in the group of hydrocolloids. From a chemical viewpoint, they are partially deacetylated chitins of different molecular weight. For the production of chitosans, chitin is used as a starting point, preferably the shell residues of crustaceans, which are available in large volumes as inexpensive raw materials. Chitin is usually firstly deprotonated here by addition of bases, demineralised by addition of mineral acids, and lastly deacetylated by addition of strong bases. Alternatively, the deacetylation can also be performed enzymatically. The molecular weights can be distributed over a broad spectrum. Types that have a mean molecular weight (weight average) of from about 800,000 to about 1,200,000 Dalton are preferably used.

Suitable chitosans are for example freely available on the market under the trade names Hydagen® CMF (about 1% by weight active substance in aqueous solution with about 0.4% by weight glycolic acid, molecular weight from about 500,000 to about 5,000,000 g/mol; Cognis), Hydamer® HCMF (chitosan deacetylated to about 80%, molecular weight from about 50,000 to about 1,000,000 g/mol, Chitinor, previously Cognis), Kytamer® PC (approximately 80% by weight of active substance in chitosan pyrrolidone carboxylate (INCI name: Chitosan PCA), Amerchol), Chitolam® NB/101 and Chitosan 90/100/A1 (chitosan deacetylated to approximately 90%; BioLog Heppe).

It has surprisingly been found that Chitosan 90/100/A1 is particularly well suited. This is attributed to a high degree of deacetylation. In accordance with a preferred embodiment of the present disclosure the chitosan has a degree of deacetylation of at least about 85%, more preferably at least about 90%. Cosmetic agents that comprise this chitosan with an organic acid and the used non-ionic propylene oxide-modified starch as film former can have styling properties that are of a comparable level to those of agents that comprise fully synthetic film formers.

In accordance with a preferred embodiment of the present disclosure, chitosan is contained in the cosmetic agent in an amount of from about 0.05% by weight to about 2% by weight, preferably from about 0.1% by weight to about 0.8% by weight, more preferably from about 0.3% by weight to about 0.7% by weight, in relation to the total weight of the cosmetic agent.

The cosmetic agents are exemplified in that the component of the film former containing chitosan is a neutralization product of chitosan with at least one organic acid, preferably a carboxylic acid. The neutralization product within the scope of the present disclosure is any product that is created by reacting chitosan with the organic carboxylic acid, i.e. the neutralization product can be produced separately prior to the production of the cosmetic agent or the neutralization product can be formed in situ during the production of the cosmetic agent.

In accordance with a preferred embodiment of the present disclosure, the organic carboxylic acid shall be selected from formic acid, acetic acid, citric acid, lactic acid, pyrrolidone carboxylic acid, tartaric acid, glycolic acid, nicotinic acid, hydroxyisobutyric acid, hydroxyisovaleric acid or mixtures of these acids, in particular lactic acid. This neutralization product can be produced for example in an aqueous medium by addition of chitosan and the corresponding organic carboxylic acid or part of the corresponding organic carboxylic acid.

It has been found that cosmetic agents that comprise film formers including a neutralization product of chitosan with the above acids, in particular with lactic acid, and a non-ionic propylene oxide-modified starch bring about styling properties which achieve a high level comparable to that of cosmetic agents comprising fully synthetic film formers.

In accordance with a preferred embodiment of the present disclosure, the ratio by weight of chitosan to the organic acid preferably lies between from about 2:1 and about 1:10, preferably between from about 1:1 and about 1:6, even more preferably between from about 1:2 and about 1:4. In this more preferred embodiment, the total weight of the used chitosan is set in relation to the total weight of the organic acid in the cosmetic agent. A particularly preferred organic acid is lactic acid. Lactic acid is a solubility improver. Used in the above ratios by weight, it results in particularly advantageous styling effects and gives the hair a particular hairstyle hold. Excellent styling properties can be obtained in particular in what are known as curl retention tests, which can be performed at high air humidity.

The second component from the group of film formers is a non-ionic propylene oxide-modified starch. Starch is a reserve carbohydrate that is stored by many plants in the form of starch grains (granules) usually from about 1 to about 200 μm in size in various plant parts, for example in tubers or roots, grain seeds, fruits and in the pith. A usable non-ionic propylene oxide-modified starch can derive from starch from potatoes, maize, rice, pea, acorn, horse chestnut, barley, wheat, banana, sago, millet, sorghum, oat, barley, rye, beans, batata, arrowroot or manioc. Particularly advantageous effects are attained by non-ionic propylene oxide-modified tapioca starch or non-ionic propylene oxide-modified potato starch or by mixtures of both aforementioned starches. The cosmetic agent very particularly preferably contains at least one non-ionic propylene oxide-modified potato starch.

Starch belongs to the family of homoglycans and is a polycondensation product of D-glucose. Here, starch includes three structurally different polymers of D-glucopyranose, specifically amylose, amylopectin and what is known as an intermediate fraction. Higher plants contain from about 0 to about 45% by weight amylose in relation to the dry substance.

The intermediate fraction, which is also referred to as abnormal amylopectin, is arranged structurally between the amylose and the amylopectin. The amount values for amylopectin defined within the scope of this application comprise the intermediate fraction.

It is preferred if the non-ionic propylene oxide-modified starch has an amylose content of less than about 25% by weight, in particular of less than about 20% by weight, in each case in relation to the weight of the modified starch. It has been found that, in order to achieve the styling properties, a starch that contains from about 17 to about 22% by weight amylose and from about 79 to about 83% by weight amylopectin is particularly suitable.

Amylose predominantly comprises linear α-1,4-glycosidically linked D-Glucose, Mw from about 50,000 to about 150,000. The resultant chains form double helices in the starch. Amylopectin, besides the α-1,4 links described for amylose, also contains α-1,6 bonds in an amount of from about 4 to about 6% as branch points. The average distance between the branch points is approximately 12 to about 17 glucose units. The molar mass of about $10^7$ to about $7 \times 10^8$ corresponds to approximately $10^5$ glucose units, whereby amylopectin belongs to the largest biopolymers. Said branchings are distributed over the molecule in such a way that a cluster structure with relatively short side chains develops. Two of these side chains in each case form a double helix. Amylopectin is relatively well soluble in water due to the many branching points.

A non-ionic propylene oxide-modified starch, as described above, is understood to mean a reaction product formed of a starch and propylene oxide. A reaction product of this kind preferably comprises at least one structural unit of formula (PS),

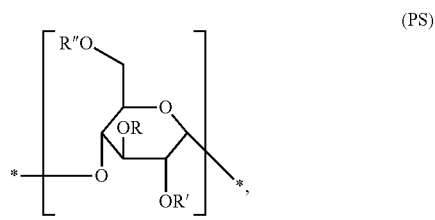

in which at least one group R, R' or R" stands for a group of formula

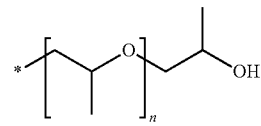

with n≤2 and at most 2 of the groups from R, R', R" stand for a hydrogen atom. A bond exemplified by the symbol "*" in formulas in this application corresponds to a free valence of the corresponding structural unit. The non-ionic propylene oxide-modified starches are provided for example by reacting a natural starch with propylene oxide. Prior to the modification with propylene oxide, the starch may have been exposed to various physical or chemical processes, such as a heat treatment, shearing, a thermal, acid-hydrolytic, oxidative or enzymatic cleaving, etc.

It is preferred if the non-ionic propylene oxide-modified starch is present in the cosmetic agent in the form of individual starch particles (granules). For this purpose, the starch particles are broken down, for example by heat or shearing, and the corresponding polysaccharide molecules are released from the composite. The released polysaccharide molecules are modified by employing propylene oxide after or prior to release.

Within the scope of a preferred embodiment, the non-ionic propylene oxide-modified starch is gelatinised. If an aqueous suspension of starch is heated or compressed, a tangential swelling of the body with loss of the birefringence, modification of the X-ray structure, and abrupt increase in viscosity of the solution is observed at a critical temperature or pressure. This appearance is referred to as gelatinisation.

The non-ionic propylene oxide-modified starches are present in the cosmetic agent in a molecular weight distribution. Preferred non-ionic propylene oxide-modified starches have a mean molecular weight of from about 50 to about 2,500 kDa (weight average). The molecular weight distribution was determined experimentally by employing gel filtration chromatography versus dextran.

Particularly preferred cosmetic agents contain non-ionic propylene oxide-modified starches that have a mean molecular weight (weight average) of from about 100 to about 2,000 kDa, in particular from about 500 to about 1,800 kDa, very particularly preferably from about 700 to about 1,000 kDa.

In order to adjust the molecular weight, the starch is subjected to a mechanical and/or a chemical treatment prior to or after the modification by employing propylene oxide. To increase the molecular weight, said starch can be cross-linked, A cross-linking of the non-ionic propylene oxide-modified starch is present when the linear or branched polysaccharide macromolecules of the starch are covalently linked by a crosslinking agent so as to form a three-dimensional, insoluble and only still swellable polymer network. Natural starch is generally un-cross-linked and—if cross-linking were desirable—requires an artificial cross-linking by employing synthesis chemistry. Such an artificial cross-linking can be performed by cross-linking agents. Non-ionic propylene oxide-modified starches that do not have a cross-linking of this kind are un-cross-linked.

A cross-linking is performed for example by the cross-linking agent epichlorohydrin. To this end, a about 42% by weight mixture of non-ionic propylene oxide-modified starch is produced in water, the desired amount of epichlorohydrin is stirred into this mixture at room temperature, and, after a stirring time of from about 1 to about 5 hours with control of the viscosity, once the target viscosity has been reached the cross-linked starch is isolated in accordance with conventional methods. It is, however, particularly preferred as contemplated herein if the cosmetic agent, as non-ionic propylene oxide-modified starch, contains at least one un-cross-linked non-ionic propylene oxide-modified starch.

In order to attain a lower molecular weight of from about 100 to about 400 kDa, said starches are preferably exposed to a mechanical cleaving, an enzymatic cleaving (in particular with alpha-amylase, beta-amylase, glucoamylase or debranching enzymes), an acid-hydrolytic cleaving (in particular with hydrochloric acid, sulfuric acid, or phosphoric acid), a thermal cleaving or a reaction with oxidising agents (such as periodate, hypochlorite, chromic acid, permanganate, nitrogen dioxide, hydrogen peroxide or organic percarboxylic acid, preferably with hydrogen peroxide). Kneaders, extruders, stator/rotor machines and/or agitators are suitable for mechanical cleaving.

The oxidative cleaving by employing hydrogen peroxide is preferred as contemplated herein. For this purpose, the non-ionic propylene oxide-modified starch is for example added to water, heated to from about 50 to about 70° C., hydrogen peroxide is added, and the mixture is stirred at from about 70 to about 85° C. for from about 2 to about 5 hours.

The content of propylene oxide in the starch affects the fine tweaking of the hairstyle hold with the hairstyle flexibility and the stability of the cosmetic agent. It has been found that the parameters are further optimised if the non-ionic propylene oxide-modified starch has a propylene oxide content of from about 1 to about 20% by weight, particularly preferably a propylene oxide content of from about 4 to about 12% by weight, very particularly preferably a propylene oxide content of from about 9.5 to about 10.5% by weight—in relation to the weight of the modified starch. The propylene oxide content can be determined for example by carrying out a Hodges cleaving by employing the method according to DIN EN 13268 (issue date 2007-06).

It has also been found that cosmetic agents as contemplated herein in which the non-ionic propylene oxide-modified starch in a about 43% by weight aqueous solution has a preferred viscosity in the range of from about 150 to about 1,500,000 mPa s (Brookfield viscometer, spindle #7 at about 20° C. and about 20 rpm) are excellently suitable. Particularly suitable non-ionic propylene oxide-modified starches have viscosities of from about 10,000 to about 200,000 mPa s, particularly preferably from about 25,000 to about 180,000 mPa s (in each case measured under the aforementioned conditions).

It is preferred if the cosmetic agent contains the non-ionic propylene oxide-modified starch in an amount of from about 0.5% by weight to about 20% by weight, preferably from about 1% by weight to about 12% by weight, more preferably from about 1% by weight to about 7% by weight, and most preferably from about 3% by weight to about 6.5% by weight, in each case in relation to the weight of the cosmetic agent.

In accordance with a preferred embodiment of the present disclosure, the cosmetic agent contains small amounts of a nourishing polymer that is particularly preferably a cationic homopolymer. Cationic polymers are understood to be polymers which in the main and/or side chain have a group which is "temporarily" or "permanently" cationic. As contemplated herein, "permanently cationic" polymers are those which comprise a cationic group irrespective of the pH value of the agent. These are generally polymers which contain a quaternary nitrogen atom, for example in the form of an ammonium group. Preferred cationic groups are quaternary ammonium groups.

In particular, homopolymers in which the quaternary ammonium groups are bonded via a C1-4 alkylene group to a homopolymer main chain constructed from acrylic acid amide, wherein the three alkyl groups besides the C1-4 alkylene group of the ammonium group are selected independently of one another from C1-10 alkyl groups, have proven to be particularly suitable.

In order to compensate for the positive polymer charge, all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, triflate.

In accordance with a particularly preferred embodiment of the present disclosure, the cosmetic agent contains, as a nourishing cationic homopolymer, poly(3-acrylamidopropyl)trimethyl ammonium chloride. The nourishing homopolymer is very particularly preferably used in an amount of from about 0.0001% by weight to about 0.2% by weight, preferably in an amount of more than from about 0.01% by weight to less than about 0.1% by weight, in relation to the total weight of the cosmetic agent. These nourishing homopolymers are indeed fully synthetic polymers, however they are used in a very small amount. Furthermore, cationic homopolymers based on acrylamide, due to their nature and according to definition, are not film formers in the conventional sense.

In accordance with a further embodiment the cosmetic agent additionally contains emulsifiers. Emulsifiers cause the formation of water-stable or oil-stable adsorption layers at the phase interface, which layers protect the dispersed droplets against coalescence and thus stabilise the emulsion. Emulsifiers are therefore constructed from a hydrophobic and a hydrophilic molecule part, similarly to surfactants. Hydrophilic emulsifiers preferably form O/W emulsions (oil-in-water emulsions) and hydrophobic emulsifiers preferably form W/O emulsions (water-in-oil emulsions). The selection of these emulsifying surfactants or emulsifiers is focused here on the substances to be dispersed and the particular outer phase and the fineness of the emulsion. O/W emulsifiers are preferred, and particularly preferred emulsifiers are addition products of from about 15 to about 60 mol ethylene oxide with castor oil and hydrogenated castor oil, in particular PEG-40 Castor Oil (INCI). The particularly preferred emulsifiers have the advantage that they can be obtained from natural, non-fully synthetic raw substance sources.

In order to intensify the effects as contemplated herein, the cosmetic agents preferably contain additionally at least one surfactant. Generally, non-ionic, anionic, cationic, and ampholytic surfactants can be contained in cosmetic products. The group of ampholytic or amphoteric surfactants comprises zwitterionic surfactants and ampholytes. It has proven to be particularly advantageous if the cosmetic agents additionally contain at least one cationic surfactant in order to increase the haircare properties.

Cationic surfactants that can be used with preference are those of the quaternary ammonium compound, esterquat and amidoamine type. Preferred quaternary ammonium compounds are ammonium halides, in particular chlorides and bromides, such as alkyl trimethyl ammonium chlorides, dialkyl dimethyl ammonium chlorides, and trialkyl methyl ammonium chlorides. The long alkyl chains of these surfactants preferably have from about 10 to about 18 carbon atoms, for example as in cetyl trimethyl ammonium chloride, stearyl trimethyl ammonium chloride, distearyl dimethyl ammonium chloride, lauryl dimethylammonium chloride, lauryl dimethyl benzyl ammonium chloride and tricetyl methyl ammonium chloride. In accordance with a preferred embodiment of the present disclosure, alkyltrimethyl ammonium salts are used, more preferably C12-C20 alkyltrimethyl ammonium salts, particularly preferably C16-C18 alkyltrimethyl ammonium chlorides, in particular cetrimonium chloride.

In a preferred embodiment of the present disclosure the cosmetic agent contains from about 0.01 to about 4% by weight, particularly preferably from about 0.1 to about 3% by weight, and in particular from about 0.2 to about 2% by weight of the cationic surfactant, wherein the amounts stated relate to the total weight of the cosmetic agent.

The application properties of the cosmetic agent can be further increased by the use of small amounts of one or more polyvalent alcohols. Preferred cosmetic agents contain one or more C3 to C12 alkane-1,2 diols, more preferably C3 to C10 alkane-1,2-diols. The cosmetic agent particularly preferably contains propane-1,2-diol and caprylyl glycol. These particularly preferred diols improve the application properties, are nourishing so to speak, and are suitable for forming a stable emulsion together with the particularly preferred emulsifier. In relation to the total weight of the cosmetic agent, the alkane-1,2-diol is contained in the cosmetic agent in an amount of from about 0.01 to about 1.5% by weight, more preferably from about 0.22 to about 0.8% by weight in a preferred embodiment of the present disclosure.

In a preferred embodiment of the present disclosure the cosmetic agent contains at least one nourishing oil. Oils are advantageous as nourishing substances since they give the hair a silky shine and make the hair more resistant by being absorbed by the hair. Nourishing oils, however, place higher demands on the product formulation, since they must be incorporated in a stable manner, without demonstrating a disadvantageous reduction or creaming during longer storage periods of product containers.

In accordance with a preferred embodiment of the present disclosure, the cosmetic agent comprises at least one nourishing oil and/or at least one nourishing constituent, more preferably at least one natural nourishing oil, i.e. a substance comprising a triglyceride of natural origin, wherein vegetable nourishing oil(s)/nourishing constituent(s) are particularly preferred. Nourishing constituents are non-polymeric in nature. Vegetable nourishing oils from the group of amaranth seed oil, argan oil, rice germ oil, baobab oil, manetti oil, marula seed oil, yangu seed oil, rambutan oil, buckthorn oil, monoi de tahiti, tigernut oil, Inca inchi oil, avocado oil, cottonseed oil, cupuacu butter, cashew oil, safflower oil, peanut oil, jojoba oil, chamomile oil, coconut oil, pumpkinseed oil, linseed oil, macadamia oil, corn seed oil, almond oil, apricot seed oil, poppy seed oil, evening primrose oil, olive oil, rapeseed oil, soya oil, sunflower oil, and wheat germ oil are particularly preferred, in particular (−)-α-bisabolol, hydrogenated jojoba oil and/or coconut oil. A particularly preferred nourishing constituent comprises the cosmetic agent D-panthenol. The advantage of these nourishing oils or nourishing constituents lies in the fact that they originate to the greatest possible extent from natural sources and are thus energy- and resource-friendly raw materials. In accordance with a preferred embodiment, the cosmetic agent can contain from about 0.0005 to about 3% by weight, preferably from about 0.001 to about 2% by weight, and particularly preferably from about 0.05 to about 1% by weight of the sum of nourishing oils and nourishing constituents, in relation to the total weight.

In further preferred embodiments of the present disclosure the cosmetic agent also contains preservatives, fragrance and optionally further additives.

The cosmetic agent contains the above-described ingredients in a cosmetic carrier that is water-based. Within the scope of the present disclosure, this is understood to mean an aqueous or aqueous-alcoholic carrier. The cosmetic agent preferably contains at least about 50% by weight, more preferably at least about 65% by weight, particularly preferably at least about 70% by weight, and in particular preferably at least about 75% by weight of water.

The cosmetic agents are preferably provided in the form of a mousse. To this end, the cosmetic agents are packaged in a dispensing device that is either a pressured gas container filled additionally with a propellant ("aerosol container") or a non-aerosol container. The pressurised gas containers with the aid of which a product is distributed via a valve by employing the internal gas pressure of the container is referred to, according to definition, as an "aerosol container". Conversely, a "non-aerosol container" according to the aerosol definition is defined as a container under normal pressure, with the aid of which a product is distributed by employing mechanical action by way of a pump system or squeezing system.

The cosmetic agents are particularly preferably provided in the form of an aerosol mousse in an aerosol container. The cosmetic agent therefore preferably additionally contains at least one propellant. In the embodiment as aerosol mousse, suitable propellants are selected for example from $N_2O$, dimethyl ether, $CO_2$, air, alkanes with from 3 to 5 carbon atoms, such as propane, n-butane, iso-butane, n-pentane and iso-pentane, and mixtures thereof. In accordance with the embodiment of an aerosol mousse, the aforesaid alkanes, mixtures of the aforesaid alkanes, or mixtures of the aforesaid alkanes with dimethyl ether are used as sole blowing agent.

Dimethyl ether, propane, n-butane, iso-butane and mixtures thereof are preferred. Mixtures of propane and butane are very particularly preferably used as sole blowing agent in a ratio by weight of propane to butane of from about 70:30 to about 15:85. These mixtures are in turn preferably used in the cosmetic agents in an amount of from about 3 to about 15% by weight—in relation to the weight of the total agent.

By employing the ratio of propellant to the other constituents of the preparations, it is possible to set the sizes of the mousse bubbles and the respective size distribution with a given spraying device. With use of conventional aerosol containers, aerosol mousse products contain the propellant preferably in amounts of from about 1 to about 35% by weight, in relation to the total product. Amounts of from about 2 to about 30% by weight, in particular from about 3 to about 15% by weight, are particularly preferred.

Very particularly preferred cosmetic agents comprise at least one of the following embodiments A) to I):

A)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former.

B)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former, and wherein the ratio by weight of chitosan to the organic acid is between from about 2:1 and about 1:10, preferably between from about 1:1 and about 1:6, even more preferably between from about 1:2 and about 1:4.

C)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former, and wherein the cosmetic agent has a degree of acetylation of at least about 85%, more preferably of at least about 90%.

D)
A cosmetic agent for temporarily reshaping keratin fibres, in particular human hair, comprising a film former and a cosmetic carrier, wherein the film former comprises at least one neutralization product of chitosan with an organic acid and at least one non-ionic propylene oxide-modified starch, wherein the cosmetic agent is substantially free of a fully synthetic film former, wherein the neutralization product of chitosan and the organic acid is contained in the cosmetic agent in an amount of from about 0.05% by weight to about 2% by weight, preferably from about 0.1% by weight to about 0.8% by weight, more preferably from about 0.3% by weight to about 0.7% by weight in relation to the total weight of the cosmetic agent and/or the non-ionic propylene oxide-modified starch is contained in the cosmetic agent in an amount of from about 0.5% by weight to about 20% by weight, preferably from about 1% by weight to about 12% by weight, more preferably from about 1% by weight to about 7% by weight and most preferably from about 3% by weight to about 6.5% by weight in relation to the total weight of the cosmetic agent.

E)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former, wherein the chitosan is contained in the cosmetic agent in an amount of from about 0.05% by weight to about % by weight, preferably from about 0.1% by weight to about 0.8% by weight, more preferably from about 0.3% by weight to about 0.7% by weight in relation to the total weight of the cosmetic agent and/or the non-ionic propylene oxide-modified starch is contained in the cosmetic agent in an amount of from about 0.5% by weight to about 20% by weight, preferably from about 1% by weight to about 12% by weight, more preferably from about 1% by weight to about 7% by weight and most preferably from about 3% by weight to about 6.5% by weight in relation to the total weight of the cosmetic agent.

F)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former, and wherein the cosmetic agent also contains one or more C3 to C12 alkane-1,2-diols, more preferably C3 to C10 alkane-1,2-diols, and/or wherein the cosmetic agent also comprises at least one nourishing oil and/or a nourishing constituent which is preferably a vegetable-based nourishing oil, particularly preferably selected from the group of α-bisabolol, coconut oil and hydrogenated jojoba oil, and/or which is preferably a nourishing constituent comprising D-Panthenol.

G)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former, and wherein the cosmetic agent also contains one or more C3 to C12 alkane-1,2-diols, more preferably C3 to C10 alkane-1,2-diols and is water-based, wherein the cosmetic agent contains an emulsifier, preferably a O/W emulsifier, in particular an ethoxylated castor oil emulsifier.

H)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former, and wherein the cosmetic agent also comprises at least one nourishing oil and/or a nourishing constituent which is preferably a vegetable-based nourishing oil, particularly preferably selected from the group of α-bisabolol, coconut oil and hydrogenated jojoba oil, and/or which is preferably a nourishing constituent comprising D-Panthenol and is water-based, wherein the cosmetic agent contains an emulsifier, preferably a O/W emulsifier, in particular an ethoxylated castor oil emulsifier.

I)
A cosmetic agent for temporarily reshaping keratin fibres, in particular human hair, comprising a film former and a cosmetic carrier, wherein the film former comprises at least one neutralization product of chitosan with lactic acid and at least one non-ionic propylene oxide-modified starch, wherein the cosmetic agent is substantially free of a fully synthetic film former and the cosmetic agent contains at least about 75% by weight water.

A second subject of the present disclosure is the use of the cosmetic agent forming the first subject of the present disclosure to temporarily reshape and/or fix the form of keratin fibres, in particular human hair.

A third subject of the present disclosure is a method for temporarily re-shaping keratin fibres, in particular human hair, exemplified in that the cosmetic agent forming the first subject of the present disclosure is applied to the keratin fibres.

It has proven to be preferred if the keratin fibres are not rinsed out after the action of the cosmetic agent forming the first subject of the present disclosure and are left on the fibres.

Features relating to preferred embodiments of the first subject of the present disclosure that are described above merely in this regard of course apply accordingly to the second and third subject as features of preferred embodiments.

The following examples are intended to explain the subject matter of the present disclosure without in any way limiting it.

Examples

The following formulation as contemplated herein was produced in an aerosol container as an aerosol mousse product:

| Raw material | E1* | E2* | E3* | E4* | E5* | E6* |
| --- | --- | --- | --- | --- | --- | --- |
| Chitosan 90/100/A1[1)] | 0.33 | 0.33 | 0.33 | | | |
| Hydagen HCMF[2)] | | | | 0.33 | 0.33 | 0.33 |
| Lactic acid | 0.33 | 0.66 | 1.0 | 0.33 | 0.66 | 1.0 |
| Non-ionic propylene oxide-modified starch[3)] | 7.0 | 7.0 | 7.0 | 7.0 | 7.0 | 7.0 |
| N-DurHance ® A 1000[4)] | 2.60 | 2.60 | 2.60 | 2.60 | 2.60 | 2.60 |
| D-Panthenol | 0.15 | 0.15 | 0.15 | 0.15 | 0.15 | 0.15 |
| Dehy quart A CA[5)] | 1.0 | 1.0 | 1.0 | 1.0 | 1.0 | 1.0 |
| PEG-40 Hydrogenated Castor Oil (INCI) | 0.25 | 0.25 | 0.25 | 0.25 | 0.25 | 0.25 |
| Sodium benzoate | 0.3 | 0.3 | 0.3 | 0.3 | 0.3 | 0.3 |
| Fragrance | 0.2 | 0.2 | 0.2 | 0.2 | 0.2 | 0.2 |
| Extrapone ® Coconut/Jojoba Butter B | 0.15 | 0.15 | 0.15 | 0.15 | 0.15 | 0.15 |
| Water | to 100 | to 100 | to 100 | to 100 | to 100 | to 100 |

*values in % by weight
[1)]Chitosan (deacetylated to >90%), BioLog Heppe
[2)]Chitosan (deacetylated to 80%), Cognis
[3)]potato starch, propylene oxide content: 12% by weight propylene oxide
[4)]polyacryl amidopropyl trimonium chloride (approximately 20% active substance)
[5)]trimethyl hexadecyl ammonium chloride (approximately 25% active substance; INCI name: Aqua (Water), Cetrimonium Chloride, Cognis)

Formulations as contemplated herein were applied in the form of an aerosol mousse to test subjects for fixing the form of a hairstyle. The hair was provided with a natural shine, a strong hold of the hairstyle, and long-lasting volume. In particular, the curl retention test, which was performed at high air humidity, demonstrated excellent properties.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for temporarily reshaping keratin fibers, comprising a film former and a cosmetic carrier, wherein the film former comprises:
   from 0.05% by weight to 2% by weight of at least one neutralisation product of chitosan with at least one organic acid, wherein the ratio by weight of chitosan to the organic acid is from 1:1 to 1:10, and
   from 0.5% by weight to 20% by weight of at least one non-ionic propylene oxide-modified starch,
wherein the cosmetic composition is substantially free from a fully synthetic film former.

2. The cosmetic composition according to claim 1, wherein the film former consists substantially of:
   at least one neutralisation product of chitosan with at least one organic acid, and
   at least one non-ionic propylene oxide-modified starch.

3. The cosmetic composition according to claim 1, wherein the at least one organic acid is formic acid, acetic acid, citric acid, lactic acid, pyrrolidone carboxylic acid, tartaric acid, glycolic acid, nicotinic acid, hydroxyisobutyric acid, hydroxyisovaleric acid, and mixtures thereof.

4. The cosmetic composition according to claim 1, wherein the at least one organic acid is lactic acid.

5. The cosmetic composition according to claim 1, wherein the ratio by weight of chitosan to the organic acid is between 1:1 and 1:6.

6. The cosmetic composition according to claim 1, wherein the ratio by weight of chitosan to the organic acid is between 1:2 and 1:4.

7. The cosmetic composition according to claim 1, wherein the cosmetic composition comprises the neutralisation product of chitosan with the organic acid in an amount of from 0.3% by weight to 0.7% by weight, in relation to the total weight of the cosmetic composition, and wherein the cosmetic composition comprises the non-ionic propylene oxide-modified starch in an amount of from 3% by weight to 6.5% by weight, in relation to the total weight of the cosmetic composition.

8. The cosmetic composition according to claim 1, wherein the cosmetic composition comprises the neutralisation product of chitosan with the organic acid in an amount of from 0.1% by weight to 0.8% by weight, in relation to the total weight of the cosmetic composition.

9. The cosmetic composition according to claim 1, wherein the cosmetic composition comprises the neutralisation product of chitosan with the organic acid in an amount of from 0.3% by weight to 0.7% by weight, in relation to the total weight of the cosmetic composition.

10. The cosmetic composition according to claim 1, wherein the non-ionic propylene oxide-modified starch is a non-ionic propylene oxide-modified tapioca starch or a non-ionic propylene oxide-modified potato starch.

11. The cosmetic composition according to claim 1, wherein the cosmetic composition comprises the neutralisation product of chitosan with the organic acid in an amount of from 0.1% by weight to 0.8% by weight, in relation to the total weight of the cosmetic composition, and wherein the cosmetic composition comprises the non-ionic propylene oxide-modified starch in an amount of from 1% by weight to 7% by weight, in relation to the total weight of the cosmetic composition.

12. The cosmetic composition according to claim 1, wherein the cosmetic composition comprises the non-ionic propylene oxide-modified starch in an amount of from 3% by weight to 6.5% by weight, in relation to the total weight of the cosmetic composition.

13. The cosmetic composition according to claim 1, wherein:

the film former consists substantially of at least one neutralisation product of chitosan with at least one organic acid, and at least one non-ionic propylene oxide-modified starch;

the at least one organic acid is lactic acid;

the non-ionic propylene oxide-modified starch is a non-ionic propylene oxide-modified tapioca starch or a non-ionic propylene oxide-modified potato starch;

the ratio by weight of chitosan to the organic acid is between 1:2 and 1:4;

the cosmetic composition comprises the neutralisation product of chitosan with the organic acid in an amount of from 0.3% by weight to 0.7% by weight, in relation to the total weight of the cosmetic composition; and the cosmetic composition comprises the non-ionic propylene oxide-modified starch in an amount of from 3% by weight to 6.5% by weight, in relation to the total weight of the cosmetic composition.

14. The cosmetic composition according to claim 13, wherein the non-ionic propylene oxide-modified starch is a non-ionic propylene oxide-modified tapioca starch.

15. The cosmetic composition according to claim 14, wherein the cosmetic composition comprises from 0.01 to 1.5% by weight of one or more C3 to C12 alkane-1,2 diols.

16. The cosmetic composition according to claim 13, wherein the cosmetic composition comprises from 0.01 to 1.5% by weight of one or more C3 to C12 alkane-1,2 diols.

17. The cosmetic composition according to claim 1, wherein the cosmetic composition comprises from 0.01 to 1.5% by weight of one or more C3 to C12 alkane-1,2 diols.

* * * * *